United States Patent
Sokurski et al.

(10) Patent No.: US 7,596,411 B1
(45) Date of Patent: Sep. 29, 2009

(54) APPARATUS AND METHOD FOR TWO-COMPONENT BIOELECTRICAL IMPEDANCE RATIO MEASURING AND MONITORING

(75) Inventors: Vadim Sokurski, Calabasas, CA (US); Nirav Dalal, Northridge, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 11/760,487

(22) Filed: Jun. 8, 2007

(51) Int. Cl.
 *A61N 1/00* (2006.01)
 *A61B 5/05* (2006.01)

(52) U.S. Cl. .................. 607/17; 607/6; 607/7; 607/11; 607/15; 600/547

(58) Field of Classification Search ................ 600/547; 607/1–38
See application file for complete search history.

(56) References Cited

U.S. PATENT DOCUMENTS

| | | |
|---|---|---|
| 4,809,697 A | 3/1989 | Causey, III et al. |
| 4,944,299 A | 7/1990 | Silvian |
| 5,311,878 A | 5/1994 | Brown et al. |
| 5,746,214 A | 5/1998 | Brown et al. |
| 5,749,369 A | 5/1998 | Rabinovich et al. |
| 5,788,643 A | 8/1998 | Feldman |
| 2002/0147475 A1 * | 10/2002 | Scheiner et al. .............. 607/17 |
| 2004/0102712 A1 * | 5/2004 | Belalcazar et al. .......... 600/547 |
| 2004/0171963 A1 * | 9/2004 | Takehara .................... 600/547 |
| 2005/0054944 A1 * | 3/2005 | Nakada et al. .............. 600/547 |
| 2005/0107719 A1 | 5/2005 | Arad (Abbound) |
| 2006/0161073 A1 * | 7/2006 | Singer et al. ................ 600/547 |

* cited by examiner

*Primary Examiner*—Max Hindenburg
*Assistant Examiner*—John Pani

(57) ABSTRACT

An implantable cardiac stimulation and rhythm management device includes an impedance measuring circuit which determines a patient's intra-thoracic impedance and the resistance and reactance components of the impedance. The device includes a microcontroller which calculates a ratio (Z/R) which equals the reactance (Z) divided by the resistance (R). The microcontroller is configured to use the calculated ratios to establish a baseline intra-thoracic fluid level, an upper bound relative to the baseline, and a lower bound relative to the baseline, and to monitor the Z/R ratio relative to the baseline and upper and lower bounds. When the Z/R ratios are outside of the established bounds, operating parameters of the stimulation and rhythm management may be altered by the microcontroller.

9 Claims, 2 Drawing Sheets

APPARATUS AND METHOD FOR TWO-COMPONENT BIOELECTRICAL IMPEDANCE RATIO MEASURING AND MONITORING

BACKGROUND OF THE INVENTION

1. Field of the Invention

The present invention relates to the field of measuring and monitoring patient body fluid levels and more particularly to measuring and long-term monitoring of body fluid accumulation with bioelectrical impedance.

2. Description of the Related Art

Pulmonary edema is a condition that results in intra-thoracic fluid accumulation, particularly accumulating within the lungs. Pulmonary edema results when the normal exchange of oxygen and carbon dioxide is disrupted by increased pressure within the blood vessels of the lungs, forcing fluid into the alveoli. Alveoli that are filled with fluid are thereby prevented from absorbing oxygen, resulting in pulmonary edema.

In most instances, heart problems are the cause of pulmonary edema, a condition often referred to as congestive heart failure (CHF). CHF is a condition in which the heart does not adequately maintain circulation of blood. CHF is characterized by an increase in thoracic fluid, particularly in the lungs wherein pulmonary edema is the result.

CHF may occur when the left ventricle of the heart cannot pump out enough of the blood received from the lungs. As a result, pressure increases inside the left atrium and then in the pulmonary veins and capillaries, causing fluid to be pushed through the capillary walls into the alveoli of the lungs. Various medical conditions and disease states exist that may cause the left ventricle to weaken and eventually fail include: coronary arty disease; cardiomyopathy; heart valve problems; and high blood pressure (hypertension).

CHF may also occur when the right ventricle is unable to overcome increased pressure in the pulmonary artery. This is normally a result from left-side heart failure, chronic lung disease or high blood pressure in the pulmonary artery (pulmonary hypertension). Persistent pulmonary edema may raise pressure in the pulmonary artery and eventually the right ventricle begins to fail. Since the right ventricle has a much thinner wall of muscle than does the left side, the increased pressure backs up into the right atrium and then into various parts of the body, including a buildup of fluid in the pleural space (pleural effusion).

Not all pulmonary edema results from heart disease. Fluid may also leak from the capillaries in the alveoli because the capillaries themselves have become more permeable, even without the buildup of back-pressure from the heart. This condition is noncardiac pulmonary edema. Some conditions or disease states that may cause noncardiac pulmonary edema include: lung infections; exposure to certain toxins such as chlorine, ammonia or nitrogen dioxide; anaphylaxis; smoke inhalation; drug overdose; acute respiratory distress syndrome; and high altitude.

Accurate assessment of this thoracic and/or pulmonary fluid accumulation is critical in assisting with diagnosing the condition and/or disease as well as monitoring the effectiveness of treatment regimens. Electrocardiography (ECG) will reveal a range of information about the heart's function, including inter alia heart rate and rhythm and whether areas of the heart may have diminished blood flow. Echocardiography is another well-known technique to assist in diagnosing heart-related problems that may contribute to pulmonary edema. Transesophageal echocardiography (TEE) may also be used to diagnose heart and central pulmonary artery problems. Cardiac catherization may be used to measure the pressure in lung capillaries.

Generally, a decrease in extracellular fluid within the lungs indicates an improvement in the condition and/or disease while an increase of extracellular fluid within the lungs indicates a worsening of the condition and/or disease.

These conventional methods either require expensive equipment and trained personnel, i.e., cardiac catheterization or echocardiography, or are simply not very accurate in monitoring intra-thoracic fluid accumulation, in particular pulmonary edema. A more accurate and non-invasive technique is highly desirable.

It has long been known in the art that changes in body fluid levels are correlated with overall body changes in impedance. Impedance is a complex quantity, consisting of a resistive or active component and a capacitive or reactive component. Bioelectrical impedance measurement and analysis is made possible by the many complex circuits of the human body, with cells and the interstitial fluid each having distinct electrical characteristics.

Cells comprise membrane-bounded chambers filled with a concentrated solution of nutrients. The cell membrane comprises a non-conductive phospholipid bilayer sandwiched between two layers of conductive protein molecules. The phospholipids are arranged tail to tail around the circumference of the cell membrane, acting as an electrical insulator. The heads of the phospholipids carry a charge, i.e., are polar, while the tails are non-polar. The cell membrane further comprises water-soluble proteins therethrough, creating pores through which water, nutrients, waste, etc., may enter into and exit from the cell. This cell membrane thus functions as a permeable barrier separating the intracellular (cytoplasm) and extracellular (interstitial) components.

The membrane-enclosed cells have electrical characteristics that may form capacitors, and thus have reactance. On the other hand, the extracellular/interstitial fluid environment in which the cells are immersed is primarily resistive in nature.

The first component of impedance, resistive or active impedance (R) is the resistance to the flow of an electric current; a characteristic shared by all substances. Reactance (Z) is the second component of impedance and is the opposition to the flow of electrical current caused by capacitance in biological tissues, particularly cell membranes. Impedance is the vector sum of resistance R and reactance Z, where reactance is the Y coordinate and resistance is the X coordinate. Thus, impedance is equal to the square root of the squared sums of the values of X and Y.

The biological tissue model wherein a cell is immersed in interstitial fluid may be analogized to an electrical circuit having a resistor (interstitial fluid) in parallel with a capacitor (cell bounded by membrane). Reactance Z is inversely proportional to frequency. Thus, reactance Z decreases as frequency increases, and as frequency decreases, reactance Z increases.

The effect of the inverse relationship of reactance and frequency on measuring impedance using the biological tissue model discussed above is that electrical current at very low frequency will not penetrate the cellular membrane, which acts as an insulator in this case. Therefore, very low frequency current passes through the extracellular/interstitial fluid, responsible for the resistive component R of impedance while the reactive or capacitive component Z of impedance will be very nearly zero.

Conversely, very high frequency current causes the capacitive cellular membrane to behave as a nearly perfect capacitor. In this case the impedance reflects a combination of both the resistive component and the reactive component.

Using this information, Subramanyan, et al. and others have shown that both the resistive and reactive components of the body's impedance to flow of a relatively high frequency electrical current may be correlated with the amount of fluid retained by a patient. As the accumulated fluid dissipates with treatment, the resistance R and reactance Z both increase as does the electrical phase angle. See Subramanyan, et al., "Total Body Water in Congestive Heart Failure", Jour. Asso. Phys. Ind., Vol. 28, September, 1980, pp 257-262; U.S. Pat. No. 5,788,643. These known techniques comprise applying electrodes to two limbs of a patient and then passing a high frequency current between the electrodes. Current, voltage and phase angle are calculated and compared with baseline values to determine whether intervention is required. However, these known techniques measure total body water and do not specifically focus on intra-thoracic or pulmonary fluid accumulation.

Moreover, known impedance measurements in patients are subject to a plurality of artifacts that affect the measurement both during a measurement timepoint (intra) and from timepoint to timepoint (inter). For example, electrode placement from measurement to measurement will differ causing impedance differences, the impedance of the skin changes over time, chest cavity impedance will change substantially, by as much as 300 percent during the respiratory cycle due to the ever-changing volume of air in the lungs, chest cavity impedance also changes by as much as 3 percent during the cardiac cycle due to the constantly changing perfusion levels of the lungs. In addition, simple movement by the patient and/or patient posture changes, both intra-measurement and inter-measurement, introduces motion artifacts that result in changes in the resistive R and reactive Z components of impedance, skewing the results.

Many complicated techniques have been proposed to eliminate the effects of impedance artifacts upon impedance measurements. For example, complex compensation techniques for changing impedance of the skin are discussed in U.S. Pat. No. 5,749,369. Temporal averaging has also been proposed, among other techniques, to eliminate the very large impedance changes due to the changing air volume in the lungs. See, e.g., Eyuboglu, B. M. et al., "In Vivo Imaging of Cardiac Related Impedance Changes," March 1989, IEEE Engineering in Medicine and Biology Magazine, Vol. 8, pp. 39-45. Moreover, U.S. Pat. No. 5,311,878 suggests numerical techniques to reduce noise in impedance measurements and U.S. Pat. No. 5,746,214 outlines use of different impedances at different electrical frequencies to assist in distinguishing between cardiac and respiratory affects. Each of these known techniques is complex, involving correction of impedance date in at least one aspect.

A more accurate method of accurately assessing impedance, and fluid accumulation, in the human thoracic cavity and lungs would be highly desirable.

BRIEF SUMMARY OF THE INVENTION

The present invention provides, in various embodiments, an improved method and apparatus for measuring and long-term monitoring of body tissue impedance within the animal thoracic cavity and/or lungs. One aspect of the invention comprises eliminating motion artifacts including motion by the patient during impedance measurement, patient posture and the like by incorporating impedance measurement capabilities into an implantable device such as cardiac pacing device. Various embodiments of the inventive method take advantage of the fact that motion artifacts equally affect the resistive R and reactive Z components of impedance. Thus, a relative ratio of the two components of impedance may be calculated and utilized to reduce and/or eliminate the negative impacts of the artifacts. In various embodiments, the present invention use of the relative ratio of reactance and resistance to assist in diagnosing fluid accumulation conditions and/or disease states and in assessing the efficacy of treatment regimens.

Advantageously, the present invention provides, in one or more embodiments, a device and method for measuring intra-thoracic fluid levels and assessing pulmonary edema without interference from motion artifacts.

Advantageously, the present invention provides, in one or more embodiments, a device and method for accurately measuring and monitoring relative changes in reactance and resistance within the animal thoracic cavity and/or lungs.

Advantageously, the present invention provides, in one or more embodiments, a device and method for accurately measuring and monitoring relative changes in reactance and resistance within the animal thoracic cavity and/or lungs and that eliminates the effect of motion artifacts on the reactance and resistance data.

Advantageously, the present invention provides, in one or more embodiments, a device and method that incorporates an impedance measuring apparatus that accurately measures and monitors changes in reactance and resistance within the animal thoracic cavity and/or lungs into an implantable device such as a cardiac pacing device.

Advantageously, the present invention provides, in one or more embodiments, a device and method that continuously measures the relative changes in reactance and resistance within the animal thoracic cavity and/or lungs and allows for intra and/or inter patient comparative analysis techniques.

Advantageously, the present invention provides, in one or more embodiments, a device and method that monitors intra-thoracic fluid levels, e.g., pulmonary edema, and automatically adjusts the stimulation provided by an implantable pacemaker/cardioverter/defibrillator (ICD) in response.

DETAILED DESCRIPTION

The following description includes the best mode presently contemplated for carrying out the invention. This description is not to be taken in a limiting sense, but is made merely for the purpose of describing the general principles of the invention. The scope of the invention should be determined with reference to the claims.

The present invention provides a method and apparatus for assessing and monitoring impedance for the purpose of assessing and monitoring fluid accumulation levels of the human thoracic cavity and/or lungs and for automatically adjusting the implantable ICD stimulation in response to long-term impedance measurements.

Figure 1:
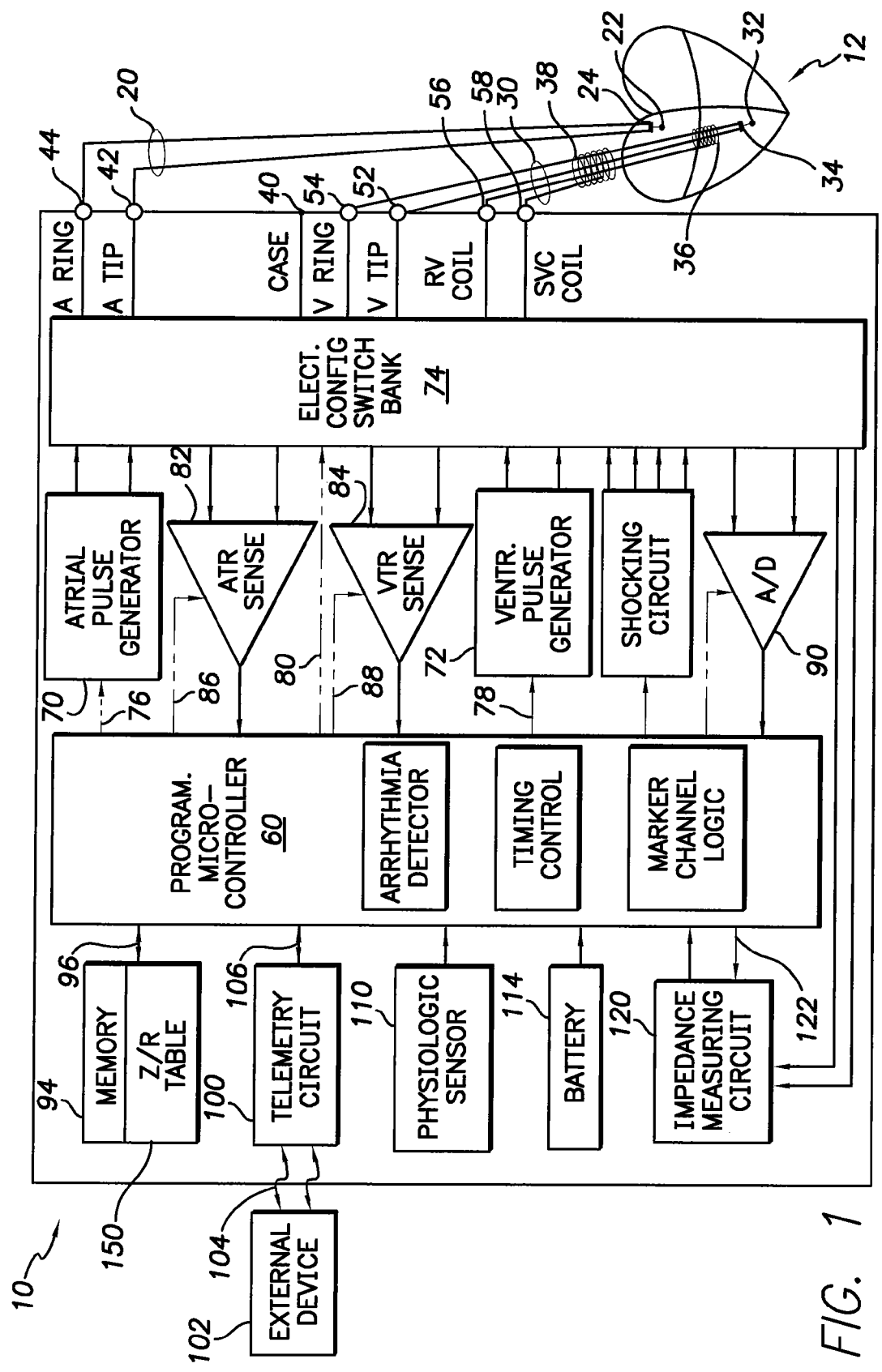
FIG. 1 is a simplified functional block diagram of an implantable pacemaker/cardioverter/defibrillator (ICD) of the present invention.

To better understand the invention, it will first be helpful to have an understanding of the basic functions performed by exemplary implantable stimulation devices with which the invention may be used, e.g., an ICD with dual chamber coils (see FIG. 1) and/or a dual-chamber pacemaker (which is a subset of that shown in FIG. 1). While a dual-chamber device has been chosen for this description, this is for teaching purposes only. It is recognized that the teachings of this invention can be used with a three or four chamber cardiac stimulation device as well as a cardiac stimulation device having multiple electrodes in one or more of its chambers.

In FIG. 1, a simplified block diagram is shown of an exemplary dual-chamber implantable cardiac stimulation device 10 which is capable of treating both fast and slow arrhythmias with stimulation therapy, including cardioversion, defibrillation, and pacing stimulation.

To provide atrial chamber pacing stimulation and sensing, the implantable cardiac stimulation device 10 is shown in electrical communication with a patient's heart 12 by way of an implantable atrial lead 20 having an atrial tip electrode 22 and an atrial ring electrode 24. The electrode pair 22 and 24 is preferably positioned in the right atrium, e.g., in the patient's atrial appendage.

The implantable cardiac stimulation device 10 is also shown in electrical communication with the patient's heart 12 by way of an implantable ventricular lead 30 having, in this embodiment, a ventricular tip electrode 32, a ventricular ring electrode 34, a right ventricular (RV) coil electrode 36, and a superior vena cava ("SVC") coil electrode 38. Typically, the ventricular lead 30 is transvenously inserted into the heart 12 so as to place the RV coil electrode 36 in the right ventricular apex, and the SVC coil electrode 38 in the superior vena cava. Accordingly, the ventricular lead 30 is capable of receiving cardiac signals and delivering stimulation in the form of pacing and shock therapy to the right ventricle.

The housing 40 (shown schematically) for the implantable cardiac stimulation device 10 includes a connector (not shown) having an atrial tip terminal 42 and an atrial ring terminal 44 which are adapted for connection to the atrial tip electrode 22 and the atrial ring electrode 24, respectively. The housing 40 further includes a ventricular tip terminal 52, a ventricular ring terminal 54, a right ventricular (RV) shocking terminal 56, and an SVC coil terminal 58, which are adapted for connection to the ventricular tip electrode 32, the ventricular ring electrode 34, the RV coil electrode 36, and the SVC coil electrode 38, respectively. The housing 40 (often referred to as the "can", "case" or "case electrode") may be programmably selected to act as the return electrode or anode alone or in combination with one of the coil electrodes, 36 and 38. For convenience, the names of the electrodes are shown next to the terminals.

At the core of the implantable cardiac stimulation device 10 is a programmable microcontroller 60 or other processor, which controls the various modes of stimulation therapy. As is well known in the art, the microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art.

As shown in FIG. 1, an atrial pulse generator 70 and a ventricular pulse generator 72 generate pacing stimulation pulses for delivery to the patient's heart by the atrial lead 20 and the ventricular lead 30, respectively, via a switch bank 74.

The pulse generators, 70 and 72, are controlled by the microcontroller 60 via appropriate control signals, 76 and 78, respectively, to trigger or inhibit the stimulation pulses as well as to determine the controlled energy level, i.e., the amplitude and/or duration of the stimulation pulses that will reliably stimulate (capture) the cardiac tissue. The microcontroller 60 further includes timing circuitry that controls the implantable cardiac stimulation device's timing of such stimulation pulses.

The switch bank 74 includes a plurality of switches for switchably connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar or bipolar) by selectively closing the appropriate combination of switches (not shown) as is known in the art.

An atrial (ATR) sense amplifier 82 and a ventricular (VTR) sense amplifier 84 are also coupled to the atrial and ventricular leads 20 and 30, respectively, through the switch bank 74 for detecting the presence of cardiac activity. It is the function of the sense amplifiers to sense the electrical activity of the heart 12, as is known in the art, such as R-waves which are the intracardiac electrogram representation of ventricular depolarizations which result in the contraction of ventricular tissue, and P-waves which are the intracardiac electrogram representation of atrial depolarizations which result in the contraction of atrial tissue. Thus, by sensing the ventricular and/or atrial depolarizations (manifested by the R-waves and/or P-waves on the intracardiac electrogram) through the sense amplifiers, the microcontroller 60 is able to make a determination as to the rate and regularity of the patient's heart beat. Such information, in turn, allows the microcontroller 60 to determine whether the patient's heart 12 is experiencing an arrhythmia, and to apply appropriate stimulation therapy. Furthermore, the amplifier 84 is typically configured to detect an evoked response from the heart 12, i.e., a response to an applied stimulation pulse, thereby aiding in the detection of "capture". Capture occurs when an electrical stimulus applied to the heart is of sufficient energy to depolarize the cardiac tissue, thereby causing the heart muscle to contract, or in other words, causing the heart to beat. Capture does not occur when an electrical stimulus applied to the heart is of insufficient energy to depolarize the cardiac tissue such that propagation of depolarization to adjacent cardiac tissue ensues. Following each capturing stimulation pulse, the associated cardiac tissue (i.e., the atria or the ventricles) enters into a physiologic refractory period during which it cannot be re-stimulated.

Alternatively, the pulse generators 70, 72 can be used to pace the heart 12 in accordance with a preselected pacing strategy. To accomplish this task, the amplitude of pacing pulses generated by the pulse generators may be set by the physician to a value above the threshold level for the patient's heart to ensure capture, i.e., successful stimulation of the patient's heart. Preferably, as described further below, the pacing pulse amplitude may be set via an automatic capture/threshold determination to ensure successful stimulation of the patient's heart 12.

The switch bank 74 determines the "sensing polarity" of the cardiac signal by selectively closing the appropriate switches, as is also known in the art. In this way, the clinician may program the sensing polarity independent of the stimulation polarity.

Each sense amplifier, 82 and 84, preferably employs a low power, precision amplifier with programmable gain and/or automatic gain control, bandpass filtering, and a threshold detection circuit, known in the art, to selectively sense the cardiac signal of interest. The automatic gain control enables the implantable cardiac stimulation device 10 to deal effectively with the problem of sensing the low frequency, low amplitude signal characteristics of ventricular fibrillation.

The outputs of the atrial and ventricular sense amplifiers, 82 and 84, are connected to the microcontroller 60, which, in turn, inhibit the atrial and ventricular pulse generators, 70 and 72, respectively, in a demand fashion whenever cardiac activity is sensed in the respective chambers. The sense amplifiers, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sense amplifiers, 82 and 84, as is known in the art.

For arrhythmia detection, the present invention may use the atrial and ventricular sense amplifiers, 82 and 84, to sense cardiac signals to determine whether a rhythm is physiologic or pathologic. As used herein "sensing" is reserved for the noting of an electrical depolarization, and "detection" is the processing of these sensed depolarization signals and noting the presence of an arrhythmia. The timing intervals between intrinsic sensed events (e.g., the P-P and R-R intervals) determine an intrinsic cardiac cycle rate that is then classified by the microcontroller 60 by comparing it to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, also known as "tiered therapy").

Cardiac signals are also applied to the inputs of an analog to digital (A/D) data acquisition system 90. The data acquisition system 90 is configured to acquire intracardiac electrogram signals, convert the raw analog data into a digital signal, and store the digital signals for later processing and/or telemetric transmission to an external device 102, e.g., an external programmer. The data acquisition system 90 is coupled to the atrial and ventricular leads, 20 and 30, through the switch bank 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the implantable cardiac stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable cardiac stimulation device 10 may be non-invasively programmed into the memory 94 through a telemetry circuit 100 in telemetric communication with the external device 102. The telemetry circuit 100 is activated by the microcontroller via control signal 106. The telemetry circuit 100 advantageously allows intracardiac electrograms and status information relating to the operation of the implantable cardiac stimulation device 10 in addition to the data contained in the memory 94 relating to the interaction of the device with the patient's heart to be sent to the external device 102 through an established communication link 104. The communication link 104 may be any suitable link such as an RF (radio frequency) channel, a magnetic link, an inductive link, an optical link, and the like. For examples of such devices, see U.S. Pat. No. 4,809,697, entitled "Interactive Programming and Diagnostic System for use with Implantable Pacemaker" (Causey, III et al.) and U.S. Pat. No. 4,944,299, entitled "High Speed Digital Telemetry System for Implantable Device" (Silvian), the entire contents of which are hereby incorporated by reference.

The implantable cardiac stimulation device 10 may further include a physiologic sensor 110. Such sensors are commonly called "rate-responsive" sensors. The physiological sensor 110 is used to detect the exercise state of the patient, to which the microcontroller 60 responds by adjusting the rate and AV delay at which the atrial and ventricular pulse generators, 70 and 72, generate stimulation pulses. A common type of rate-responsive sensor is an activity sensor, such as an accelerometer or a piezoelectric crystal, which is mounted within the housing 40 of the implantable cardiac stimulation device 10. Other types of physiologic sensors are also known, for example, sensors which sense the oxygen content of blood, respiration rate and/or minute ventilation, pH of blood, ventricular gradient, etc. However, any sensor may be used which is capable of sensing a physiological parameter which corresponds to the exercise state of the patient.

The implantable cardiac stimulation device 10 additionally includes a battery 114 which provides operating power to all of the circuits shown in FIG. 1. For the implantable cardiac stimulation device 10, the battery 114 must be capable of operating at low current drains for long periods of time, and, in the case where the pacemaker also performs as a cardioverter/defibrillator (ICD), the battery must also be capable of providing high-current pulses (for capacitor charging) when the patient requires a shock pulse. The battery 114 must also have a predictable discharge characteristic so that elective replacement time can be detected. Accordingly, the present invention preferably employs lithium/silver vanadium oxide batteries, as is presently true for many such devices.

The implantable cardiac stimulation device 10 further may include a magnet detection circuitry (not shown) coupled to the microcontroller 60. It is the purpose of the magnet detection circuitry to detect when a magnet is placed over the implantable cardiac stimulation device 10, which magnet may be used by a clinician or patient to perform various functions controlling the implantable cardiac stimulation device 10.

As further shown in FIG. 1, the present invention may include an impedance measuring circuit 120, which is enabled by the microcontroller 60 by a control signal 122. The known uses for the impedance measuring circuit 120 include, but are not limited to, lead impedance surveillance during the acute and chronic phases for proper lead positioning or dislodgment, detecting operable electrodes and automatically switching to an operable pair if dislodgment occurs, measuring respiration or minute ventilation, measuring thoracic impedance for determining shock thresholds, detecting when the device has been implanted, measuring stroke volume, and detecting the opening of the valves, etc. The impedance measuring circuit 120 is advantageously coupled to the switch bank 74 so that any desired electrode (including the RV and SVC coil electrodes, 36 and 38) may be placed in communication with impedance measuring circuit 120 and may thus be used to measure impedance components R and Z according to the present invention.

Figure 2:
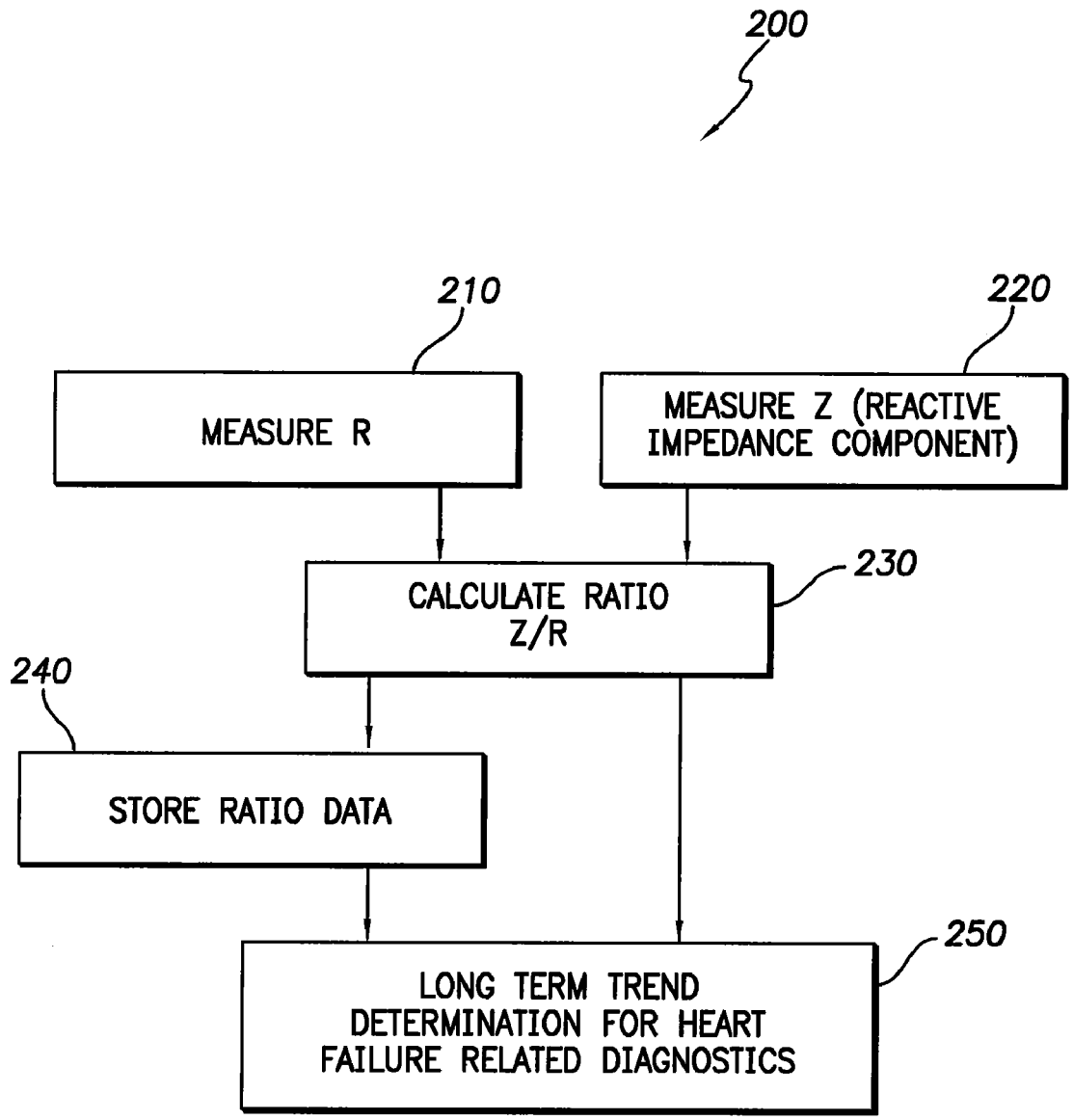
FIG. 2 is a simplified top level flow diagram of the impedance measuring method of the present invention.

Turning now to FIG. 2, one embodiment of the present inventive method is illustrated. Initially, the resistive R and reactive Z components of impedance are measured 210, 220. Measurements 210, 220 are accomplished using impedance measuring circuit 120 as discussed above. As illustrated in FIG. 1, the microcontroller 60 may store modifiable impedance measurement instructions for both the resistive component R and the reactive component Z. Microcontroller 60 is in communication with memory 94, where non-invasive programming may be programmed into memory 94 through telemetry circuit 100 in telemetric communication with external device 102 as discussed above.

Memory 94 may further allow impedance measurement data to be stored therein, for example in table 150 where the resistive R and the reactive Z components of impedance may be separately stored by measurement timepoint for further review and/or data manipulation.

Referring again to FIG. 2, the relative ratio of Z and R is calculated 230 as Z/R. The impedance component data stored within table 150 may be provided to microcontroller 60 for relative ratio calculation and/or provided to external device 102 through telemetry circuit 100 for review and/or data manipulation and relative ratio calculation. Alternatively, a relative ratio of the measurement data Z and R may be calculated by microcontroller 60 immediately upon measurement, wherein the results of the calculation, i.e., the relative ratio, is then provided to memory 94 for storage within table 150 and/or to external device 102 for storage and/or review.

In any event, the relative ratio Z/R data is stored according to the present invention 240, either within memory 94 and/or within external device 102. Subsequently, the relative ratio data may be used to assist in identifying, evaluating and determining long-term trends in heart failure-related diagnostics providing, e.g., an early view of increasing intra-thoracic fluid levels and/or pulmonary edema.

For example, the long-term relative ratio data may be used to establish a baseline fluid level for a given patient. Since the electrodes are at a fixed position on the cardiac stimulation device, and measurement of impedance components Z and R occurs virtually continuously in various embodiments of the present invention, adverse impacts of motion and other artifacts are virtually eliminated. The microcontroller 60 and/or external device 102 may use commonly known statistical techniques to establish a baseline for a healthy patient as well as upper and lower bounds to account for normal variation in fluid levels over time. Such upper and lower bounds are most preferably calculated based on data observed and stored from the patient having the cardiac stimulation device implanted therein. Alternatively, the upper and lower bounds may be default values drawn from a "normal" population of individuals.

If the relative ratio consistently, i.e., over the long-term, trends upwardly or downwardly outside the upper and lower bounds, the microcontroller 60, external device 102, and/or patient's physician monitoring the data may cause the implanted cardiac stimulation device to change at least one of the operating parameters to bring the relative ratio data back within the upper and lower bounds, thus potentially eliminating undesirable fluid accumulation. Operating parameters that may be changed or affected include, inter alia, pacing pulse amplitude, pulse duration, rate, amplitude, waveshape and/or vector of each shocking pulse to be delivered by the cardiac stimulation device to the patient's heart. Such stimulation change instruction may occur automatically, e.g., automatically modifying programmable operating parameters initiated by the microcontroller or the external device, or alternatively may require manual intervention by a physician or other caregiver.

The description of the invention including its applications and advantages as set forth herein is illustrative and is not intended to limit the scope of the invention, which is set forth in the claims. Variations and modifications of the embodiments disclosed herein are possible and practical alternatives to, and equivalents of, the various elements of, the embodiments would be understood to those of ordinary skill in the art upon study of this patent document. These and other variations and modifications of the embodiments disclosed herein may be made without departing from the scope and spirit of the invention.

What is claimed is:

1. An implantable cardiac stimulation and rhythm management device for measuring intra-thoracic fluid impedance comprising:
   at least one impedance measuring electrode;
   an impedance measuring circuit coupled to, and in communication with, the at least one impedance measuring electrode, wherein the at least one measuring electrode is operative to measure resistive (R) and reactive (Z) components of impedance;
   a microcontroller connected to the impedance measuring circuit and configured to calculate ratios (Z/R) that equal the reactive components divided by the resistive components Z/R values has; and
   a memory connected to the microcontroller and the impedance measuring circuit and operative to store the measured reactive (Z) and resistive (R) components and the ratios;
   wherein the microcontroller is further configured to directly monitor the calculated ratios over a period of time to establish a baseline intra-thoracic fluid level for the patient and an upper bound relative to the baseline and a lower bound relative to the baseline, wherein the upper bound and the lower bound account for normal variations in intra-thoracic fluid levels over time for the patient, and to continue to directly monitor the calculated ratios relative to the baseline, upper bound and lower bound.

2. The implantable cardiac stimulation and rhythm management device of claim 1, wherein the memory is further operative to store programmable operating parameters related to cardiac stimulation used by the microcontroller.

3. The implantable cardiac stimulation and rhythm management device of claim 2, further comprising an external device connected to the microcontroller and operative to receive the measured reactive (Z) and resistive (R) components and the calculated ratios.

4. The implantable cardiac stimulation and rhythm management device of claim 3, wherein the external device is further operative to modify the cardiac stimulation operating parameters stored in the memory based on the measured reactive (Z) and resistive (R) components and the calculated ratios.

5. The implantable cardiac stimulation and rhythm management device of claim 4, further comprising a telemetry circuit in communication with the external device and the microcontroller.

6. The implantable cardiac stimulation and rhythm management device of claim 1, wherein the at least one impedance measuring electrode comprises at least one of the group consisting of ventricular tip electrode, ventricular ring electrode, right ventricular coil electrode, and superior vena cava electrode.

7. The implantable cardiac stimulation and rhythm management device of claim 1, wherein the microcontroller is operative to determine if one of the ratios is located inside or outside the established upper bound and lower bound.

8. The implantable cardiac stimulation and rhythm management device of claim 7, wherein the memory is further operative to store programmable operating parameters related to cardiac stimulation used by the microcontroller and the microcontroller is operative to automatically modifying at least one of the cardiac stimulation operating parameters in response to the location of the ratios.

9. The implantable cardiac stimulation and rhythm management device of claim 2, wherein the microcontroller is further operative to modify the cardiac stimulation operating parameters stored in the memory based on the measured reactive (Z) and resistive (R) components and calculated ratios.

* * * * *